(12) United States Patent
Mahajan et al.

(10) Patent No.: US 9,737,228 B2
(45) Date of Patent: Aug. 22, 2017

(54) PHYSIOLOGIC EVENT DETECTION AND DATA STORAGE

(71) Applicant: Cardiac Pacemakers, Inc., St. Paul, MN (US)

(72) Inventors: Deepa Mahajan, Roseville, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/007,307

(22) Filed: Jan. 27, 2016

(65) Prior Publication Data

US 2016/0220139 A1    Aug. 4, 2016

Related U.S. Application Data

(60) Provisional application No. 62/109,963, filed on Jan. 30, 2015.

(51) Int. Cl.
| | |
|---|---|
| *A61B 5/00* | (2006.01) |
| *A61B 5/0452* | (2006.01) |
| *A61N 1/362* | (2006.01) |
| *A61N 1/37* | (2006.01) |
| *A61B 5/024* | (2006.01) |

(Continued)

(52) U.S. Cl.
CPC ............ *A61B 5/0452* (2013.01); *A61B 5/686* (2013.01); *A61B 5/7264* (2013.01); *A61B 5/7282* (2013.01); *A61N 1/3622* (2013.01); *A61N 1/3702* (2013.01); *A61B 5/0245* (2013.01); *A61B 5/02405* (2013.01); *A61B 5/046* (2013.01); *A61B 5/04012* (2013.01);

(Continued)

(58) Field of Classification Search
CPC ..... A61B 5/0452; A61B 5/686; A61B 5/7264; A61B 5/7282; A61N 1/3702
See application file for complete search history.

(56) References Cited

U.S. PATENT DOCUMENTS

| | | | |
|---|---|---|---|
| 7,031,765 B2 | 4/2006 | Ritscher et al. | |
| 7,421,292 B1 | 9/2008 | Kroll | |

(Continued)

FOREIGN PATENT DOCUMENTS

WO    WO-2016123161 A1    8/2016

OTHER PUBLICATIONS

Krueger, Jonathan Walter, et al., "Atrial Fibrillation Detection Using Ventricular Rate Variability", U.S. Appl. No. 62/037,348, filed Aug. 14, 2014.

(Continued)

*Primary Examiner* — Robert N Wieland
(74) *Attorney, Agent, or Firm* — Schwegman Lundberg & Woessner, P.A.

(57) ABSTRACT

Systems and methods for detecting a target physiologic event and storing physiologic information associated with the detected physiologic event are disclosed. A system can receive a physiologic signal obtained from a subject, and detect the target physiologic event using a first portion of the received physiologic signal. The system can confirm the target physiologic event using a second portion of the received physiologic signal. If the target physiologic event is confirmed, the system can store physiologic information associated with the confirmed target physiologic event in a memory.

20 Claims, 4 Drawing Sheets

(51) Int. Cl.
    *A61B 5/0245*     (2006.01)
    *A61B 5/04*     (2006.01)
    *A61B 5/046*     (2006.01)
    *A61B 5/0464*     (2006.01)

(52) U.S. Cl.
    CPC ........... *A61B 5/0464* (2013.01); *A61B 5/7275* (2013.01); *A61N 1/3627* (2013.01)

(56) References Cited

U.S. PATENT DOCUMENTS

| | | |
|---|---|---|
| 2006/0094972 A1 | 5/2006 | Drew |
| 2010/0106033 A1* | 4/2010 | Lian .................. A61B 5/02405 600/509 |
| 2010/0305642 A1 | 12/2010 | Dong et al. |
| 2014/0236029 A1 | 8/2014 | Averina et al. |

OTHER PUBLICATIONS

"International Application Serial No. PCT/US2016/015013, International Search Report mailed Apr. 18, 2016", 5 pgs.

"International Application Serial No. PCT/US2016/015013, Written Opinion mailed Apr. 18, 2016", 5 pgs.

\* cited by examiner

PHYSIOLOGIC EVENT DETECTION AND DATA STORAGE

CLAIM OF PRIORITY

This application claims the benefit of priority under 35 U.S.C. §119(e) of U.S. Provisional Patent Application Ser. No. 62/109,963, filed on Jan. 30, 2015, which is herein incorporated by reference in its entirety.

TECHNICAL FIELD

This document relates generally to medical devices, and more particularly, to devices and methods for detecting physiologic event and storing physiologic data.

BACKGROUND

Implantable medical devices (IMDs) have been used for monitoring patient health condition or disease states and delivering therapies. For example, implantable cardioverter-defibrillators (ICDs) can be used to monitor for certain abnormal heart rhythms and to deliver electrical energy to the heart to correct the abnormal rhythms. Some IMDs can be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

The IMDs can be programmed to store measured physiologic data in a memory. These physiologic data can be retrieved and presented to a system user such as a clinician in a display device. The system user can review the stored physiologic data to determine the presence or causes of a physiologic event, or to determine whether a device therapy results in desired therapeutic outcome.

Some IMDs are able to detect cardiac arrhythmias, such as atrial fibrillation (AF). AF is the most common clinical arrhythmia affecting millions of people. During AF, disorganized electrical pulses originated from regions in or near an atrium can lead to irregular conductions to ventricles, thereby causing inappropriately fast and irregular heart rate. AF can be paroxysmal that may last from minutes to days before it stops by itself, persistent that may last for over a week and typically requires medication or other treatment to revert to normal sinus rhythm, or permanent where a normal heart rhythm cannot be restored with treatment. Timely detection of AF, and storing electrograms and other physiologic information associated with the AF, can be clinically important for assessing progression of AF.

OVERVIEW

Implantable medical devices are capable of detecting physiologic events, such as cardiac arrhythmias or progression of chronic heart diseases, and obtaining sampled values of cardiac electrical activity signals such as electrograms. Some IMDs can further be communicated with multiple physiologic sensors that can measure various physiologic signals. The IMD can be programmed to monitor and store data sensed from some or all of the physiologic sensors.

Capturing accurate electrogram or other physiologic sensor information obtained over a longer period of time, such as chronically between regularly-scheduled outpatient office visits, can help the physician re-program the device, if needed, or to diagnose and assess the patient's condition. However, recording of electrograms or other physiologic sensor data can be limited by the restricted data storage space available within the IMB. For example, in an IMD that is programmed to detect AF event and More long electrogram episode or other physiologic data associated with AF, the memory of the IMB can be quickly exhausted. On the other hand, some portions of the stored data associated with the detected AF may not represent characteristics of AF, such as due to the paroxysmal nature of the detected AF episode, or due to the lack of specificity in detecting the AF event. Storing non-characteristic AF data not only wastes memory, but can also be confusing for clinicians reviewing the stored data with little diagnostic or analytical value.

Memory limitations in IMDs can negatively impact the overall design and functionality of the IMDs. As such, retaining collected electrograms and other physiological data and presenting it in a meaningful manner to a clinician can present challenges in IMDs. Merely providing more data storage space in the IMD may not be ideal in improving the efficiency of memory usage. The present inventors have recognized, among other things, substantial challenges and a demand for more efficient memory usage, while storing as much most clinically relevant physiologic data associated with a physiologic event as possible.

This document discusses, among other things, a system for detecting a target physiologic event and storing physiologic information associated with the detected physiologic event. The system can receive a physiologic signal obtained from a subject, and detect the target physiologic event using a first portion of the received physiologic signal. The system can comprise a data storage decision circuit that can confirm the target physiologic event using a second portion of the received physiologic signal. The second portion can include part of the first portion of the received physiologic signal. The data storage decision circuit can generate a data storage trigger signal upon the detection and the confirmation of the target physiologic event. In response to the data storage trigger signal, the system can store physiologic information associated with the confirmed target physiologic event in a memory.

In Examples 1, a system can comprise a signal receiver circuit that can receive a physiologic signal obtained from a subject. The system can also comprise a physiologic event detector circuit that can detect a target physiologic event using a first portion of the received physiologic signal, and a data storage decision circuit coupled to the signal receiver circuit and the physiologic event detector circuit. The data storage decision circuit can be configured to confirm the target physiologic event using a second portion of the received physiologic signal, where the second portion can include at least part of the first portion of the received physiologic signal. The data storage decision circuit can also generate a data storage trigger signal using the detection and the confirmation of the target physiologic event. The system can include a controller circuit, coupled to the data storage decision circuit, that can store in a memory physiologic information associated with the confirmed target physiologic event in response to the data storage trigger signal. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

In Example 2, the first portion of the received physiologic signal of Example 1 can include a first data window of the received physiologic signal, and the second portion can include a second data window temporally located at a specified location with the first data window.

In Example 3, the second data window of Example 2 can be temporally located within a latter half of the first data window.

In Example 4, the first portion of the received physiologic signal of Example 1 can include a first data window of the received physiologic signal, and the second portion can include second two or more non-identical data windows each temporally located at a respectively specified location within the first data window.

In Example 5, at least one of the second two or more data windows of Example 4 can overlap in time with at least another one of the second two or more data windows.

In Example 6, the data storage decision circuit of any one of Examples 4 or 5 can produce the confirmation of the physiologic event using one or more partial confirmation indications each generated using respective one of the second two or more data windows of the received physiologic signal.

In Example 7, the signal receiver circuit of any one of Examples 1 through 6 can be configured to receive the physiologic signal including a signal indicative of heart rate (HR) or cardiac interval (CI).

In Example 8, the signal receiver circuit of Example 7 can be coupled to a sensor that can be configured to sense cardiac electrical or mechanical activity. The signal receiver circuit can generate the signal indicative of the HR or the CI using the cardiac electrical or mechanical activity.

In Example 9, the physiologic event detector circuit of any one of Examples 1 through 8 can be configured to classify cardiac intervals within the first portion of the received physiologic signal into one of first two or more beat classes. Each of the first two or more beat classes can include respective beat count. The physiologic event detector circuit can detect the target physiologic event in response to the beat counts of the first two or more beat classes meeting a specified criterion.

In Example 10, the first two or more beat classes of Example 9 can include two or more of a stable beat class, an unstable beat class, or a random beat class. The physiologic event detector circuit can detect the target physiologic event in response to a relative quantity among the beat counts of the first two or more beat classes falling within a specified range, the relative quantity including a ratio or a proportion.

In Example 11, the physiologic event detector circuit of Example 10 can compute a beat variability for each of the cardiac intervals within the first portion, and classify the cardiac intervals within the first portion into one of the stable beat class, the unstable beat class, or the random beat class when the beat variability falls within a specified range.

In Example 12, the data storage decision circuit of any one of Examples 1 through 11 can classify cardiac intervals within the second portion of the received physiologic signal into one of second two or more beat classes. Each of the second two or more beat classes can have a respective beat count. The data storage decision circuit can further generate the data storage trigger signal in response to the beat counts of the second two or more beat classes meeting a specified criterion.

In Example 13, the physiologic information of any one of Examples 1 through 12, which are associated with the confirmed target physiologic event, can include the second portion of the received physiologic signal.

In Example 14, the data storage decision circuit of any one of Examples 1 through 13 can be configured to track time elapsed from a previous data storage trigger signal, and can generate the data storage trigger signal further in response to the elapsed time exceeding a specified threshold.

In Example 15, the physiologic event detector circuit of any one of Examples 1 through 14 can be configure to detect the target physiologic event including a cardiac arrhythmia or progression of a chronic disease.

In Example 16, a method can comprise steps of receiving a physiologic signal obtained from a subject, detecting a target physiologic event using a first portion of the received physiologic signal, generating a confirmation indication of the target physiologic event using a second portion of the received physiologic signal. The second portion can include at least part of the first portion of the received physiologic signal. The method can comprise generating a data storage trigger signal using the detection and the confirmation of the target physiologic event, and storing in a memory in response to the data storage trigger signal, physiologic information associated with the confirmed target physiologic event.

In Example 17, the first portion of the received physiologic signal of Example 16 can include a first data window of the received physiologic signal. The second portion can include a second data window temporally located at a specified location within the first data window.

In Example 18, the step of receiving the physiologic signal of Example 16 can include receiving a signal indicative of heart rate (HR) or cardiac interval (CI).

In Example 19, the step of detecting the target physiologic event of Example 16 can include detecting a cardiac arrhythmia or progression of a chronic disease. An example of the cardiac arrhythmia includes an atrial fibrillation (AF) event.

In Example 20, the step of detecting a target physiologic event of Example 16 can include computing cardiac cycles within the first data window of the received physiologic signal, classifying the cardiac cycles into one of first two or more beat classes, each of the first two or more beat classes including a respective beat count, and detecting the target physiologic event can include detecting the target physiologic event in response to the beat counts of the first two or more beat classes meeting a specified criterion.

In Example 21, the first two or more beat classes of Example 20 can include two or more of a stable beat class, an unstable beat class, or a random beat class. The step of detecting the target physiologic event of Example 20 can include computing a relative quantity among the counts of the first two or more beat classes, and detecting the target physiologic event in response to the relative quantity falling within a specified range, where the relative quantity can include a ratio or a proportion.

In Example 22, the step of generating a confirmation indication of the target physiologic event of Example 16 can include computing cardiac cycles within the second portion of the received physiologic signal, and classify the cardiac cycles into one of second two or more beat classes, each of the second two or more beat classes including a respective beat count. The step of generating the data storage trigger signal of Example 16 can include generating the data storage trigger signal in response to the beat counts of the second two or more beat classes meeting a specified criterion.

In Example 23, the first portion of Example 16 can include a first data window of the received physiologic signal, and the second portion of Example 16 can include second two or more non-identical data windows each temporally located at a respectively specified location within the first data window. The step of generating the confirmation indication of Example 16 can include generating one or more partial confirmation indications using respective one of the second two or more data windows of the received physiologic signal, and generating the confirmation indicating using a fusion of the one or more partial confirmation indications.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting a target physiologic event and storing physiologic information associated with the target physiologic event. The target physiologic event, such as an atrial fibrillation (AF) episode, can be detected using a first portion of a physiologic signal. The target physiologic event can be confirmed using a second portion of the physiologic signal. Upon the confirmation of the target physiologic event, a data storage trigger signal can be generated, which can trigger the storage of physiologic information associated with the confirmed target physiologic event in a memory.

Figure 1:
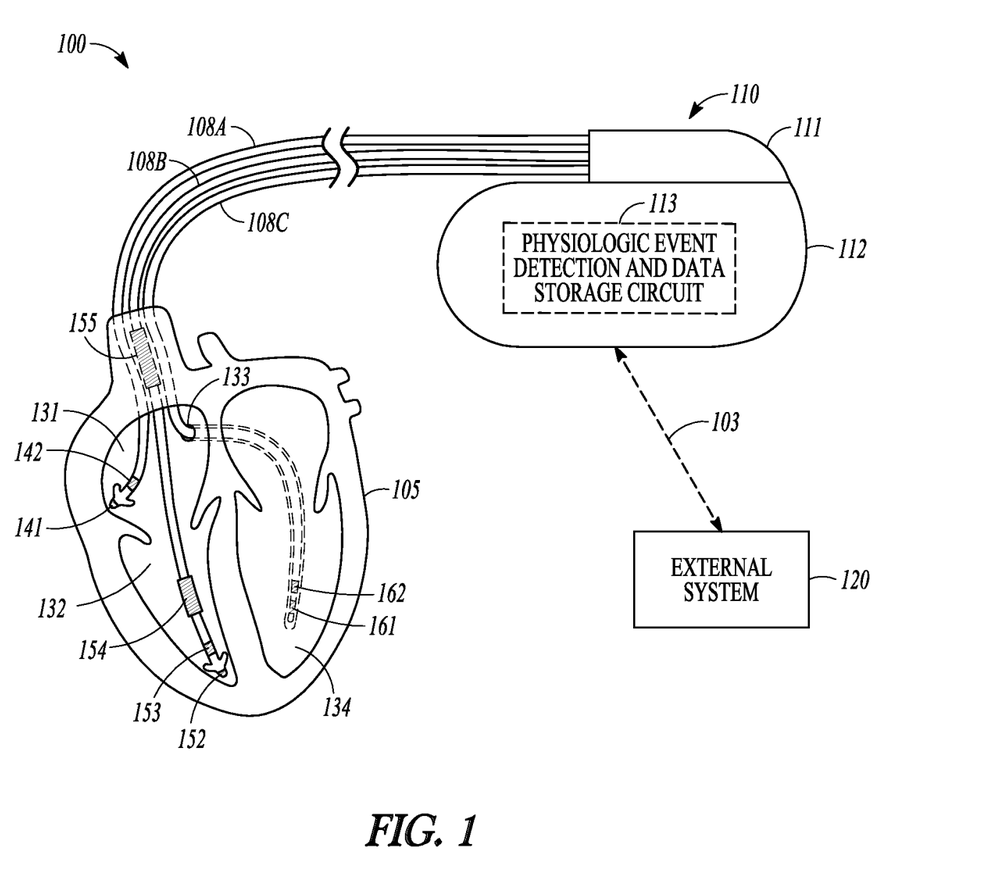
FIG. 1 illustrates an example of a Cardiac Rhythm Management (CRM) system and portions of an environment in which the CRM system can operate.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). Additionally or alternatively, the IMD 110 can include one or more monitoring or therapeutic devices such as a subcutaneously implanted device (e.g., a subcutaneous ICD), a wearable external device, a neural stimulator, a drug delivery device, a biological therapy device, a diagnostic device, an implantable loop recorder, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV. Additional electrodes can be included in or along the lead 108C. In an example (not shown in FIG. 1), at least one of the leads 108A-C, or an additional lead other than the leads 108A-C, can be implanted under the skin surface without being within a heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMB 110 can also be configured to sense a physiological signal from one or more external physiologic sensors or one or more external electrodes that can be coupled to the IMB 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a physiologic event detection and data storage circuit 113. The physiologic event detection and data storage circuit 113 can be configured to detect a target physiologic event, such as a cardiac arrhythmia or worsening of cardiac performance, and trigger storage of physiologic information in a memory such as in the IMD or an external storage device. The physiologic event detection and data storage circuit 113 can detect the target physiologic event using a first portion of the physiologic signal, and confirm the detected target physiologic event using a different second portion of the physiologic signal. In response to the detection and confirmation of the target physiologic event, physiologic event detection and data storage circuit 113 can produce a data storage trigger signal. One or more physiologic signals or device diagnostic data can be stored to the memory in response to the data storage trigger signal. Examples of the physiologic event detection and data storage circuit 113 are described below, such as with reference to FIGS. 2-4.

The external system 120 can allow for programming of the IMB 110 and can receive information about one or more signals acquired by IMB 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMB operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The physiologic event detection and data storage circuit 113 can be implemented at the external system 120 such as using data extracted from the IMB 110 or data stored in a memory within the external system 120. Portions of the physiologic event detection and data storage circuit 113 may be distributed between the IMD 110 and the external system 120.

Portions of the IMD 110 or the external system 120 can be implemented using hardware, software, or any combination of hardware and software. Portions of the IMB 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
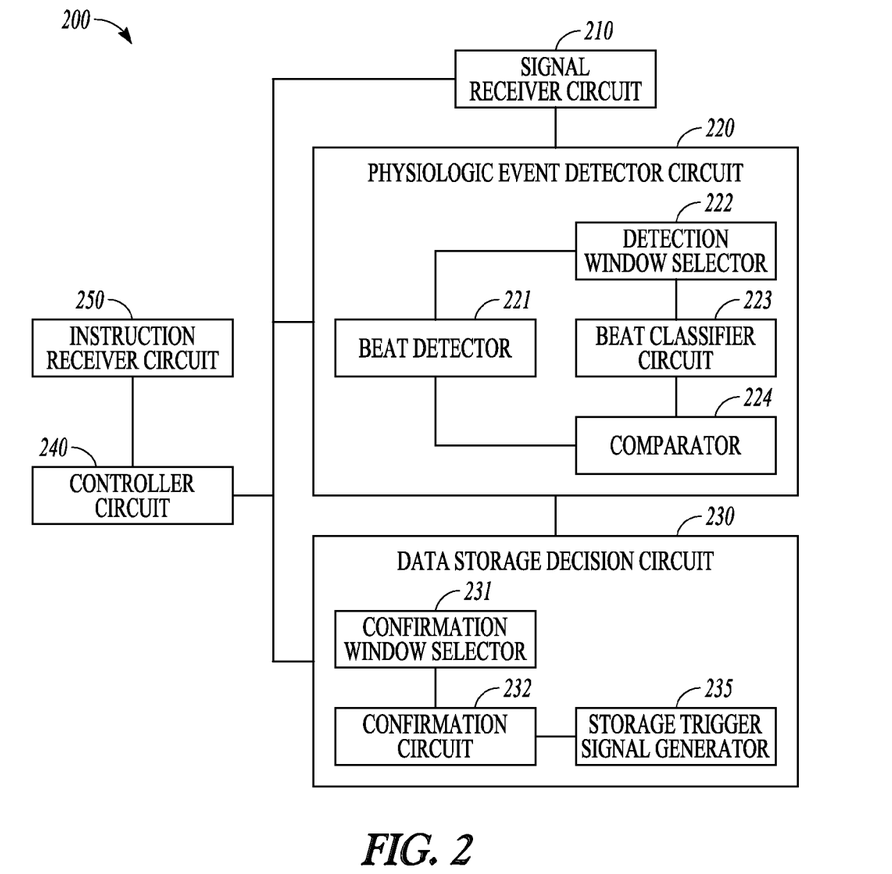
FIG. 2 illustrates an example of a physiologic event detection and data storage circuit.

FIG. 2 illustrates an example of a physiologic event detection and data storage circuit 200, which is an embodiment of the physiologic event detection and data storage circuit 113. The physiologic event detection and data storage circuit 200 can include one or more of a signal receiver circuit 210, a physiologic event detector circuit 220, a data storage decision circuit 230, a controller circuit 240, and an instruction receiver circuit 250.

The signal receiver circuit 210 can be configured to receive one or more physiological signals obtained from a patient. The physiologic signals can be indicative or correlative of a disease state or a physical or physiologic condition. The physiologic signals can be sensed using one or more implantable, wearable, or otherwise ambulatory sensors associated with the patient. Examples of the physiological signals can include surface electrocardiography (ECG) such as sensed from electrodes on the body surface, subcutaneous ECG such as sensed from electrodes placed under the skin, intracardiac electrogram (EGM) sensed from the one or more electrodes of the leads 108A-C or the can 112, heart rate signal, heart rate variability signal, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others.

In an example, the signal receiver circuit 210 can retrieve from an electronic medical record (EMR) system one or more patient historical physiologic signals in response to a command signal. The command signal can be issued by a system user (e.g., a health-care professional) such as via an input device coupled to the instruction receiver 250, or generated automatically by the system in response to a specified event. The signal receiver circuit 210 can include one or more sub-circuits that can perform signal conditioning or pre-processing, including signal amplification, digitization, or filtering, on the one or more physiological signals.

The physiologic event detector circuit 220 can be configured to detect, by using at least a portion of the sensed physiologic signal, a target physiologic event. The target physiologic event can include various acute physiologic events such as cardiac arrhythmias. Examples of cardiac arrhythmias can include atrial fibrillation (AF), atrial flutter (AFL), atrial tachycardia, paroxysmal supraventricular tachycardia (PSVT), Wolff-Parkinson-White (WPW) syndrome, ventricular tachycardia, ventricular fibrillation, bradycardia, among others. The target physiologic event can also include progression of a chronic disease, such as worsening of heart failure (HF) or HF decompensation event in a specified timeframe, such as within approximately 1-6 months, or beyond 6 months. Other examples of the target physiologic events can include pulmonary edema, pulmonary condition exacerbation, asthma and pneumonia, myocardial infarction, dilated cardiomyopathy, ischemic cardiomyopathy, systolic HF, diastolic HF, valvular disease, renal disease, chronic obstructive pulmonary disease (COPD), peripheral vascular disease, cerebrovascular disease, hepatic disease, diabetes, anemia, depression, among others.

The physiologic event detector circuit 220 can detect the target physiologic event by analyzing the cardiac electrical or mechanical activities. As illustrated, the physiologic event detector circuit 220 can include a beat detector 221, a detection window selector 222, a beat classifier circuit 223, and a beat counts comparator 224.

The beat detector 221 can be configured to detect pulsatile activity of the heart, hereinafter referred to as "beats", from the received physiologic signal. In an example, the beats can be detected using a cardiac electrical signal such as a surface ECG, a subcutaneous ECG, or an intracardiac EGM. The beat detector 221 can detect from the cardiac electrical signal one or more signal features such as a P wave, an R wave, a T wave, a QRS complex, or other components representing depolarization, hyperpolarization, repolarization, or other electrophysiological activities of the myocardium. In another example, the beats can be detected using a cardiac mechanical signal indicative of pulsatile contraction of the heart. Examples of cardiac mechanical signal can include a cardiac impedance signal, a heart sounds signal, or a blood pressure signal, among others. The cardiac mechanical signals can vary within a cardiac cycle, and exhibit a pulsatile pattern consistent with the periodic cardiac electrical activities. The beat detector 221 can detect from the cardiac mechanical signals one or more signal features, such as peak or trough amplitude, peak value of an envelope or an integral, or other intensity measures of the cardiac impedance, heart sounds, or blood pressure signals.

The beat detector 221 can use the detected signal features from the received physiologic signal to generate a cardiac interval (CI) or heart rate (HR) signal. The CI can be computed as an interval between adjacent signal features from the received physiologic signals (such as an interval between adjacent R waves, between adjacent S1 heart sounds, or between adjacent peak thoracic impedance values). The HR, in a unit of beats per minute (bpm), can be computed using the CI (in a unit of seconds) as HR=60/CI bpm.

The beat detector 221 can also produce other temporal information such as relative timing of a signal feature with respect to a reference time. For example, the beat detector 221 can compute parameters indicative of electro-mechanical delay using a signal feature of a cardiac electrical signal and a signal feature of a cardiac mechanical signal. Examples of the electro-mechanical delay can include a systolic timing interval (STI) such as measured between the onset of the QRS complex on the ECG or the atrial activation event in an intracardiac EGM and the S2 heart sound, a pre-ejection period (PEP) such as measured between the onset of the QRS and the S1 heart sound, a diastolic timing interval (DTI) such as measured between the S2 heart sound and the onset of the QRS complex on the ECG or the atrial activation event in an intracardiac EGM of the next cardiac cycle.

The detection window selector 222 can determine a first portion of the received physiologic signal for use in detecting the target physiologic event. In an example, the first portion includes a first data window ($W_D$) of the received physiologic signal. The first data window $W_D$, having a length of $L_{WD}$, can be initiated at a specified time, on a regular basis during a monitoring process, or upon a detection of a specified window activation signal. In an example of detecting an AF event, a rate of change ($\Delta X/\Delta t$) of cardiac intervals, heart rate, or other signal features can be detected within a time interval (e.g., 1-5 seconds) or within a plurality of beats (e.g., 3-10 beats). The detection window $W_D$ can begin when $\Delta X/\Delta t$ falls below a specified threshold, indicating a sudden change of the signal feature. The length of the detection window, $L_{WD}$, can be determined such as to detect sustentation of the target physiologic event (as oppose to a transient physiologic event). For example, in detecting an AF event, $L_{WD}$ can be approximately 400-800 beats. In another example, $L_{WD}$ can be approximately 5-10 minutes. In an example, the first portion includes a union of two or more different data windows of the received physiologic signal.

The beat classifier circuit 223, coupled to the beat detector 221 and the detection window selector 222, can be configured to classify the beats inside the detection window $W_D$ into one of first two or more pre-defined beat classes using the signal features such as produced by the detection window selector 222. The first two or more beat classes can each be defined by a respective value-range of a signal feature. For example, the first two or more beat classes can be based on intensity of the signal features, or based on temporal information such as cardiac intervals.

The beat classes can include a stable beat class, an unstable beat class, and a random beat class. In an example, the first two or more beat classes can be based on variability of a signal feature, such as variability of cardiac interval (CI). The variability of CI can be computed as beat-to-beat difference, i.e., $\Delta CI(i)=CI(i)-CI(i-1)$, where $CI(i)$ denotes the cardiac interval at beat "i" and $CI(i-1)$ denotes the cardiac interval at the previous beat "i-1". Alternatively, variability of the heart rate (HR) can be computed such as $\Delta HR(i)=HR(i)-HR(i-1)$, where $HR(i)=60/CI(i)$ bpm and $HR(i-1)=60/CI(i-1)$ bpm. A beat can be classified as a stable beat if $\Delta CI(i)$ or $\Delta HR(i)$ falls within a first range, such as $|\Delta HR(i)|\leq 5$ bpm. A beat can be classified as an unstable beat if $\Delta CI(i)$ or $\Delta HR(i)$ falls within a second range, such as $|\Delta HR(i)|>5$ bpm. A beat can be classified as a random beat if $CI(i)<CI(i-1)$ and $\Delta HR(i)<-5$ bpm.

In another example, the beat classes, such as one or more of stable beats, unstable beats, or random beats, can be based on two or more variability measures, such as a first ventricular rate change of a first pair of heart rates or cardiac intervals, and a second ventricular rate change of a second pair of heart rates or cardiac intervals, such as that disclosed in the commonly assigned Krueger et al. U.S. Patent Application Ser. No. 62/037,348, entitled "ATRIAL FIBRILLATION DETECTION USING VENTRICULAR RATE VARIABILITY," filed Aug. 14, 2014, which is hereby incorporated by reference in its entirety, including its disclosure of generating and presenting information about ventricular rate change information based on temporally adjacent ventricular heart beats. In an example, the beat classes can be based on $\Delta CI(i)$ and $\Delta CI(i+1)$, or based on $\Delta HR(i)$ and $\Delta HR(i+1)$, where $\Delta CI(i+1)=CI(i+1)-CI(i)$ and $\Delta HR(i+1)=HR(i+1)-HR(i)$. A beat can be classified as a stable beat if $\Delta CI(i)$ or $\Delta HR(i)$ falls within a first range and $\Delta CI(i+1)$ or $\Delta HR(i+1)$ falls within a second range, such as $|\Delta HR(i)|<5$ bpm and $|\Delta HR(i+1)|<5$ bpm. A beat can be classified as an unstable beat if $\Delta CI(i)$ or $\Delta HR(i)$ falls within a third range and $\Delta CI(i+1)$ or $\Delta HR(i+1)$ falls within a fourth range, such as $|\Delta HR(i)|>5$ bpm and $|\Delta HR(i+1)|>5$. A beat can be classified as a random beat if $\Delta HR(i)<-5$ bpm and $\Delta HR(i+1)<-5$ bpm.

The comparator 224 can be configured to compare the classified beats in the beat classes to produce a detection indication of the target physiologic event. In an example, the comparator 224 can compute, among beat counts in the beat classes, one or more relative quantities such as a difference, a ratio, a proportion, or a percentage. A detection indication of the target physiologic event can be generated when the one or more relative quantities meet their respective criterion. For example, in detecting an AF event, the comparator 224 can use the beat count of the stable beat class ($N_S$), beat count of the unstable beat class ($N_U$), and beat count of the random beat class ($N_R$) to compute a first ratio between $N_U$ and $N_S$ (i.e., $N_U/N_S$), and a second ratio between $N_R$ and a sum of $N_S$ and $N_U$ (i.e., $N_R/(N_S+N_U)$). An AF event is deemed detected if the first ratio exceeds a first detection threshold $TH_{D1}$, and the second ratio exceeds a second detection threshold $TH_{D2}$. An example of $TH_{D1}$ is approximately between 3 and 5. An example of $TH_{D2}$ is approximately between 1-10%.

The data storage decision circuit 230 can be coupled to the signal receiver circuit 210 and the physiologic event detector circuit 220. The data storage decision circuit 230 can include a confirmation window selector 231, a confirmation circuit 232, and a storage trigger signal generator 235.

The confirmation window selector 231 can determine a second portion of the received physiologic signal for use in confirming the target physiologic event. The second portion can be a subset of the first portion of the received physiologic signal used for detecting the target physiologic event. In an example, the second portion can include data from the received physiologic signal outside the first portion. In an example, the first portion includes a detection window ($W_D$), and the second portion can include a confirmation window ($W_R$) with a length of $L_{WR}$. The $L_{WR}$ can be shorter than $L_{WD}$, such that $W_R$ is completely within the detection window $W_D$. In an example, the confirmation window $W_R$ can start after the end of the detection window $W_D$.

The confirmation window $W_R$ can be initiated at a specified time such that $W_R$ can be temporally located at a specified location within $W_D$. In an example, $W_R$ can be temporally located within a latter half of $W_D$. For example, the $W_D$ can include 500 cardiac intervals of the physiologic signal, and $W_R$ can include the last 100 cardiac intervals of $W_D$.

In an example, the second portion can include two or more confirmation windows. A confirmation decision of the target physiologic event can be individually made using respective confirmation window. The two or more confirmation windows can be temporally located within the detection window $W_D$. Examples of multiple confirmation windows are discussed below, such as with reference to FIGS. 3-4.

The confirmation circuit 232 can confirm the target physiologic event using the second portion of the received physiologic signal. The confirmation circuit 232 can execute an algorithm for confirming the target physiologic event that has a higher sensitivity or a higher specificity than the algorithm such as used by the physiologic event detector circuit 220 in detecting the physiologic event. In an example, the confirmation circuit 232 can classify the beats within the second portion of the received physiologic signal (such as within the confirmation window $W_R$) into one of second two or more pre-determined beat classes each defined by a respective range of a signal feature. The second two or more beat classes can includes one or more of the first two or more beat classes. For example, the second beat classes can include one or more of the stable beat classes, unstable beat classes, or random beat classes, which are based on variability or pattern of cardiac cycles, as discussed above with respect to beat classifier circuit 223. Alternatively or additionally, the second two or more beat classes can include at least one beat class different than the first two or more beat classes. For example, the second two or more beat classes can be obtained by comparing a characteristic heart rate (such as a central tendency of the heart rates in the second portion of the received physiologic signal) to one or more threshold values.

The classified beats in the second two or more beat classes can be used to compute one or more relative quantities, such as discussed above with respect to the comparator 224 for detecting the target physiologic event. For example, in confirming a detected AF event, the confirmation circuit 232 can compute a first ratio between the beat count in the unstable beat class $N_U$ and the beat count in the stable beat class $N_S$ (i.e., $N_U/N_S$) and a second ratio between the beat count in the random beat class $N_R$ and a sum of $N_S$ and $N_U$ (i.e., $N_R/(N_S+N_U)$). An AF event is confirmed if the first ratio exceeds a first confirmation threshold $TH_{R1}$, and the second ratio exceeds a second confirmation threshold $TH_{R2}$. In an example, the confirmation thresholds ($TH_{R1}$ or $TH_{R2}$) can be approximately identical to the corresponding detection thresholds ($TH_{D1}$ or $TH_{D2}$). In another example, at least one of the confirmation thresholds can be different than the corresponding detection threshold. In an example, $TH_{D1}$ is approximately 3, and $TH_{R1}$ is approximately 5, while both $TH_{D2}$ and $TH_{R2}$ can be approximately 6%.

Alternatively or additionally, the confirmation circuit 232 can use signal features and associated criteria different than those used for detecting the target event to confirm the detected physiologic event. These additional or alternative signal features and criteria are selected such that the confirmation process has a higher sensitivity or a higher specificity than the detection process. In an example, the confirmation circuit 232 can confirm the detected physiologic event using other relative quantities, such as ratios, among the beat counts in various beat classes. In an example, the confirmation circuit 232 can use intensity or temporal features different than those used for target event detection. In another example, the confirmation window selector 231 can determine the second portion from a physiologic signal different than the signal used by the physiologic event detector circuit 220, and the confirmation circuit 232 can use signal features from the different physiologic signal to confirm the target physiologic event. For example, the confirmation circuit 232 can use characteristics of P waves of an ECG, or signal features obtained from a heart sound signal, impedance signal, or other physiologic signals for confirmation of the target physiologic event.

The storage trigger signal generator 235 can be configured to generate a data storage trigger signal using the detection and the confirmation of the target physiologic event. The data storage trigger signal can be used to activate storage of a specified portion of the received physiologic signal, such as the first portion or the second portion used respectively for detecting or confirming the target event. In an example, the data storage signal can be generated upon detecting both the detection indication of the target event from the physiologic event detector circuit 220 and a confirmation indication from the confirmation circuit 230. In another example, the data storage decision circuit 230 can further include a timer/clock circuit that tracks time elapsed ($T_{Trigger}$) from a previous data storage trigger signal. The storage trigger signal generator 235 can generate the data storage trigger signal further in response to the elapsed time exceeding a specified threshold. As an example, if the elapsed time $T_{Trigger}$ exceeds approximately 3-10 days, then a data storage trigger signal can be generated as long as the target event is detected, even if no confirmation is received. In another example, the storage trigger signal generator 235 can be programmed to attempt to generate a data storage trigger signal at a specified time or frequency, such as once every day.

In an example, the physiologic event detection and data storage circuit 200 can optionally include a therapy circuit coupled to the confirmation circuit 232. The therapy circuit can be configured to automatically program one or more therapy parameters using at least the confirmation of the detected physiologic event such as produced by the confirmation circuit 232, and deliver the therapy to a target tissue site. Examples of the therapy can include electric pacing therapy, cardioversion therapy, defibrillation therapy, neurostimulation therapy, or any other stimulation therapy using a specified energy source. In an example, the therapy circuit can automatically program and deliver an AF therapy in response to the detection and confirmation of an AF event. Examples of the therapy parameters can include pulse amplitude, pulse waveform, pulse frequency, pulse width, duty cycle, duration, or any other parameters associated with the electrostimulation.

In various examples, one or both of the physical event detector circuit 220 and the data storage decision circuit 230 can be implemented as a part of a microprocessor circuit in the physiologic event detection and data storage circuit 200. The microprocessor circuit can be a dedicated processor such as a digital signal processor, application specific integrated circuit (ASIC), microprocessor, or other type of processor for processing information including heart rates or cardiac intervals. Alternatively, the microprocessor circuit can be a general purpose processor that can receive and execute a set of instructions of performing the functions, methods, or techniques described herein.

The controller circuit 240 can receive external programming input from the instruction receiver circuit 250 to control the operations of the signal receiver circuit 210, the physiologic event detector circuit 220, the data storage decision circuit 230, and the data flow and instructions between these components and respective subcomponents. Examples of the instructions received by instruction receiver 240 can include parameters for sensing and processing the physiologic signals, detecting and classifying beats, selecting the first portion and detecting the target physiologic event in the first portion of the signal, and selecting the second portion and confirming the target physiologic event in the second portion of the signal.

The controller circuit 240 can also be configured to store physiologic information associated with the confirmed target physiologic event in response to the data storage trigger signal. The physiologic information can include specified portion of the received physiologic signal, such as the first or second portion of the received physiologic signal used respectively for target event detection and confirmation. In an example, the physiologic information can include physical or physiologic data different from the received physiologic signal, diagnostic data, or device functionality or performance data associated with the detected and confirmed physiologic event. In an example, information about the detection of confirmation of the target event can be stored together with the physiologic information. The controller circuit 240 can store the physiologic information in a memory such as within the IMD 110. Alternatively or additionally, the controller circuit 240 can control a communication circuit in transmitting the physiologic information to a specified implantable or external memory such as in a server, a database, or a patient management system for further processing or retrievably reviewed by a clinician. The transmission can be achieved through a programmer, a communicator, or any type of mobile device.

The instruction receiver circuit 250 can include a user interface configured to present programming options to a system user, and receive the system user's programming input. In an example, the controller circuit 240 can receive external user command from the instruction receiver circuit 250 that modifies, augments, or overrides the data storage trigger signal determined based on the detection and confirmation of target event. In an example, at least a portion of the instruction receiver circuit 250, such as the user interface, can be implemented in the external system 120.

Figure 3:
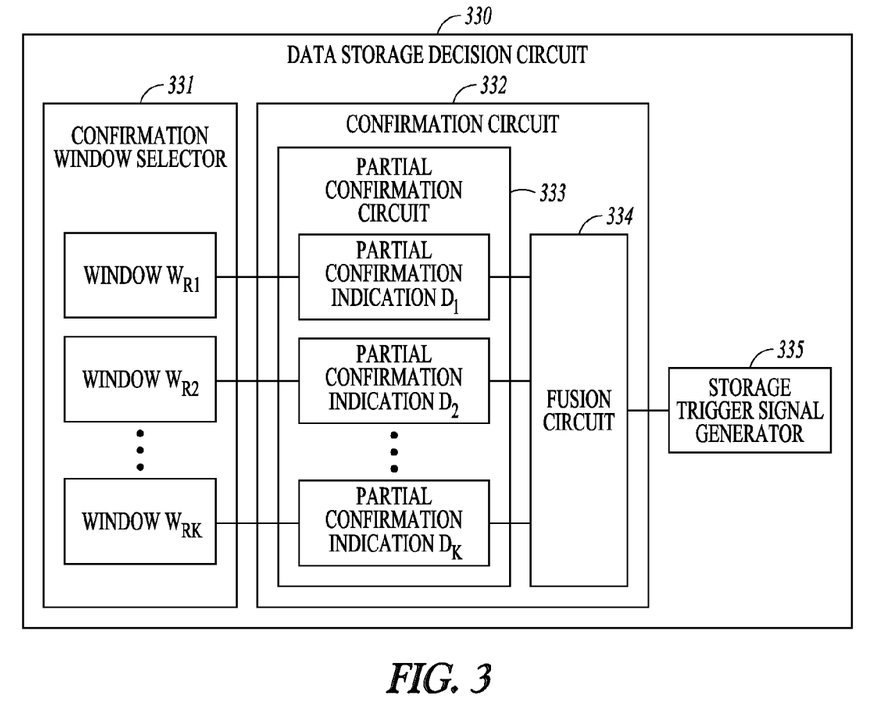
FIG. 3 illustrates an example of a multi-phase confirmation and data storage decision circuit.

FIG. 3 illustrates an example of a multi-phase confirmation and data storage decision circuit 330, which can be an embodiment of the data storage decision circuit 230. The multi-phase confirmation and data storage decision circuit 330 can include a confirmation window selector 331, a confirmation circuit 332, and a storage trigger signal generator 335.

The confirmation window selector 331 can be configured to generate two or more non-identical confirmation windows, such as K confirmation windows $W_{R1}$, $W_{R2}$, ..., $W_{RK}$. Each confirmation window, $W_{Ri}$, can be taken within, and temporally located at a specified location of, the first data window $W_D$ used for detecting the target event. In an example, at least one confirmation window can be located within the latter half of $W_D$. The beginning or the length of each confirmation window $W_{Ri}$ can be respectively determined using a method such as discussed above with respect to the confirmation window selector 231.

The length of the K confirmation windows can be identical or different. The K confirmation windows can span from the beginning to the end of the detection window $W_D$, such as by sweeping through the $W_D$. In an example, at least one confirmation window, $W_{Rp}$, overlaps in time with at least another one confirmation window $W_{Rq}$. In another example, no two confirmation windows overlap in time.

The confirmation circuit 332 can be configured to confirm the detected target physiologic event in multiple phases. The confirmation circuit 332 can include a partial confirmation circuit 333 and a fusion circuit 334. The partial confirmation circuit 333 can generate a plurality of partial confirmation indication $D_1$, $D_2$, ..., $D_K$ using the physiologic data in the respective confirmation windows $W_{R1}$, $W_{R2}$, ..., $W_{RK}$. In an example, the confirmation circuit 332 can use the method as discussed above with respect to the confirmation circuit 232 to produce the confirmation indications $D_1$ through $D_K$.

The fusion circuit 334 can be configured to use one or more partial confirmation indications, selected from $D_1$, $D_2$, ..., $D_K$, to produce the confirmation indication of the physiologic event. In an example, the confirmation indication can be a linear combination, such as a weighted sum, of the one or more partial confirmation indications. In another example, the confirmation indication can be a nonlinear combination of the one or more partial confirmation indications, such as decision trees, neural network, Bayesian network, among other machine learning methods.

The storage trigger signal generator 335, which can be an embodiment of the storage trigger signal generator 235, can be configured to generate a data storage trigger signal in response to the confirmation indication produced by the fusion circuit 334 meeting a specified criterion. As discussed above with reference to the data storage decision circuit 230, the data storage trigger signal can be generated further in response to the elapsed time from a previous data storage trigger signal exceeding a specified threshold, at a specified time or frequency, or according to an external user command, such as from the instruction receiver circuit 250, that modifies, augments, or overrides the data storage trigger signal.

Figure 4:
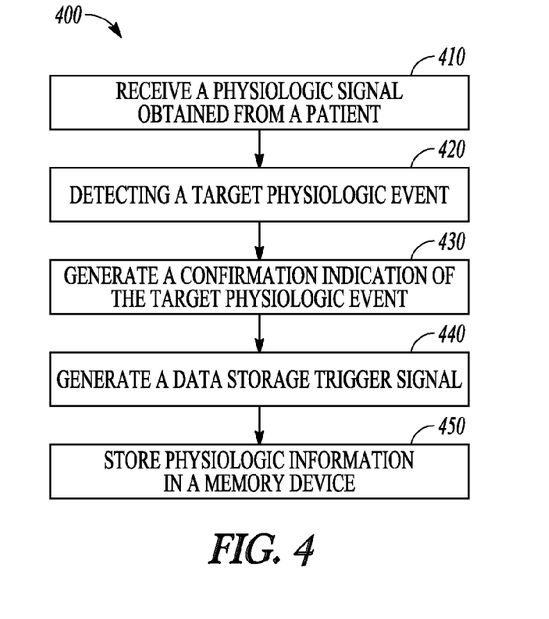
FIG. 4 illustrates an example of a method for detecting a target physiologic event and storing physiologic information in a memory.

FIG. 4 illustrates an example of a method 400 for detecting a target physiologic event and storing physiologic information in a memory. The method 400 can be implemented and operate in an implantable, wearable, or other ambulatory medical device, or in a remote patient management system. In an example, the method 400 can be performed by the physiologic event detection and data storage circuit 200, or any modification thereof.

The method 400 can begin at step 410, where a physiologic signal, such as obtained from a patient, can be received. The physiologic signals can be sensed using one or more implantable, wearable, or otherwise ambulatory sensors associated with the patient. The physiologic signals can be indicative or correlative of a disease state or a physical or physiologic condition. Examples of the physiological signals can include electrocardiography (ECG), intracardiac electrogram (EGM) such as sensed from an implantable device, heart rate signal, heart rate variability signal, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The physiologic signal can be pre-processed before being used for detecting a target event, including signal amplification, digitization, or filtering, among other signal conditioning processes.

At 420, a target physiologic event can be detected using at least a portion of the sensed physiologic signal. The target physiologic event can include various acute physiologic events or chronic diseases. In an example, the target physiologic event can include a cardiac arrhythmia, such as an atrial fibrillation (AF), an atrial flutter (AFL), an atrial tachycardia, a paroxysmal supraventricular tachycardia (PSVT), a Wolff-Parkinson-White (WPW) syndrome, a ventricular tachycardia, a ventricular fibrillation, a bradycardia, among others. In an example, the detection of the target physiologic event can include generating one or more signal features from the first portion of the sensed physiologic signal, such as amplitude or other intensity or morphological measures of ECG, EGM, thoracic impedance, heart sounds, or blood pressure. In another example, the signal features include temporal information of a signal feature with respect to a reference time. Examples of detecting the target physiologic event using a first portion of a physiologic signal are discussed below, such as with reference to FIG. 5.

At 430, a confirmation indication of the target physiologic event can be generated. In an example, the confirmation can be based on analysis of a second portion of the received physiologic signal different than the first portion used for detecting the target physiologic event. In an example, the second portion can be a subset of the first portion of the received physiologic signal. In an example, the second portion can include data from the received physiologic signal outside the first portion. In another example, the second portion can include two or more confirmation windows temporally located within the detection window. A partial confirmation of target physiologic event can be individually determined using the physiologic data in the corresponding confirmation window. The confirmation can be based on an algorithm that has a higher sensitivity or a higher specificity than the algorithm in detecting the physiologic event. In an example, the confirmation can involve alternative or additional signal features and associated criteria different than those used for detecting the target event. Examples of the confirming the target physiologic event based on a different second portion of a physiologic signal are discussed below, such as with reference to FIG. 5.

At 440, a data storage trigger signal can be generated. The data storage trigger signal can be used to activate storage of physiologic information including a specified portion of the received physiologic signal. In an example, the data storage signal can be generated upon detecting both the detection indication of the target event and the confirmation indication. Additionally or alternatively, the data storage trigger signal can be generated in response to an elapsed time from a previous data storage trigger signal exceeding a specified threshold. For example, if the elapsed time $T_{Trigger}$ exceeds approximately 3-10 days, then a data storage trigger signal can be generated as long as the target event is detected, even if no confirmation is received. In another example, a data storage trigger signal can be generated at a specified time or frequency, such as once every day. In an example, an external user command can be used to modify, augment, or override the data storage trigger signal determined based on the detection and confirmation of target event.

At 450, physiologic information can be stored in a memory, such as in response to the data storage trigger signal. The physiologic information can include specified portion of the received physiologic signal, such as the first or second portion of the received physiologic signal used respectively for target event detection and confirmation. In an example, the physiologic information can include physical or physiologic data different than the received physiologic signal, diagnostic data, or device functionality data associated with the detected and confirmed physiologic event. In an example, information about the detection of confirmation of the target event can be stored together with the physiologic information. The physiologic information can be stored in a memory in an implantable or external memory. Alternatively or additionally, the physiologic information can be transmitted to an implantable or external memory through a communication network.

Figure 5:
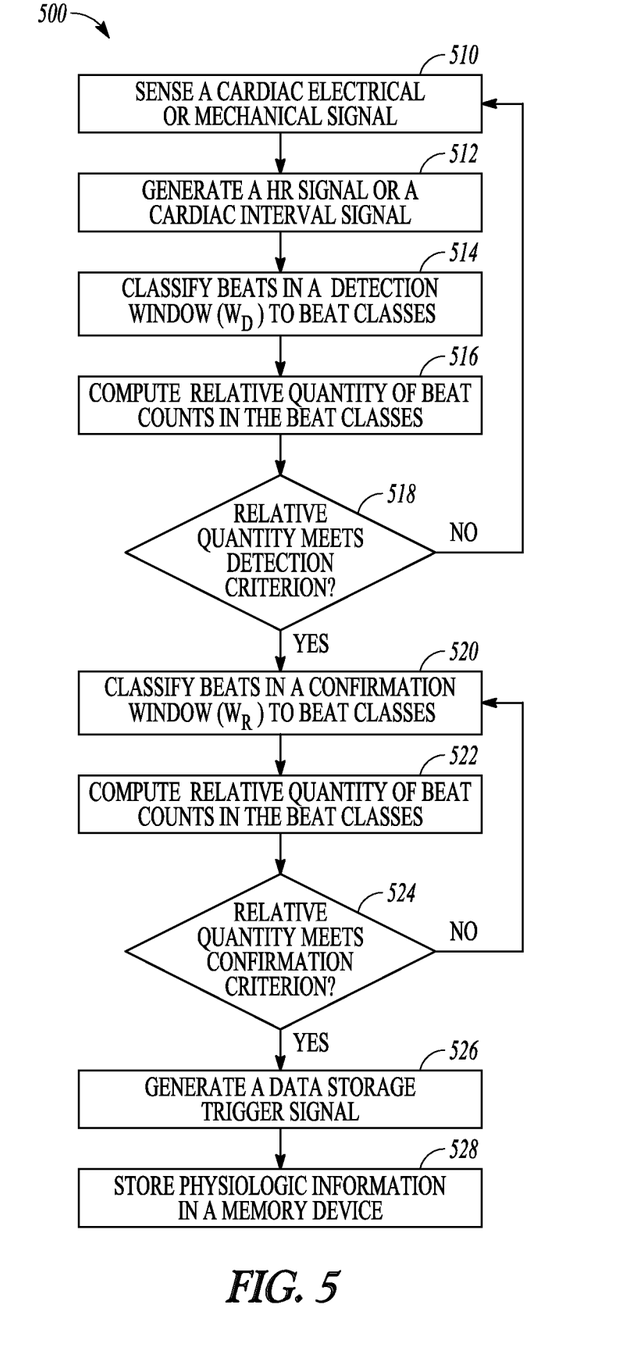
FIG. 5 illustrates an example of a method for detecting an atrial fibrillation (AF) event and storing physiologic information in a memory.

FIG. 5 illustrates an example of a method 500 for detecting an atrial fibrillation (AF) event and storing physiologic information associated with the detected AF event in a memory. The method 500 can be an embodiment of the method 400. The method 500 begins at step 510, where a cardiac electrical or mechanical signal indicative of pulsatile contraction of the heart can be sensed. The cardiac electrical or mechanical signal can include surface ECG, subcutaneous ECG, intracardiac EGM, or other physiologic signals such as thoracic impedance, heart sounds, blood pressure, among others.

At 512, pulsatile activity of the heart, i.e., the "beats", can be detected from the sensed physiologic signal, and a heart rate (HR) or a cardiac interval (CI) signal can be computed using the sensed beats. To detect the beats, one or more signal features can be detected from the cardiac electrical or mechanical signals. Examples of the signal features can include a P wave, an R wave, a T wave, a QRS complex, or other components representing depolarization, hyperpolarization, repolarization, or other electrophysiological properties of the myocardium, peak or trough amplitude of the physiologic signal, peak value of an envelope or an integral, or other intensity or morphological features generated from a cardiac impedance signal, a heart sound signal, a blood pressure signal, among other physiologic signals. The CI or HR signal then be computed using timing of the detected signal features. For example, the CI can be computed as an interval between adjacent signal features from the received physiologic signals, and the HR, in a unit of beats per minute (bpm), can be computed using the CI (in a unit of seconds) as HR=60/CI bpm. In an example, temporal information, such as relative timing of a signal feature with respect to a reference time, can be generated. For example, an electromechanical delay (EMD) can be computed such as by using one or more features from a cardiac electrical signal and one or more features from a cardiac mechanical signal. Examples of the EMD can include a systolic timing interval (STI) such as measured between the onset of the QRS complex on the ECG or the atrial activation event in an intracardiac EGM and the S2 heart sound, a pre-ejection period (PEP) such as measured between the onset of the QRS and the S1 heart sound, a diastolic timing interval (DTI) such as measured between the S2 heart sound and the onset of the QRS complex on the ECG or the atrial activation event in an intracardiac EGM of the next cardiac cycle.

At 514, beats within a specified detection window, $W_D$, can be analyzed and classified into one of first two or more pre-defined beat classes. The detection $W_D$ can begin at specified time, on a regular basis during a monitoring process, or upon a detection of a specified window activation signal. For example, in detecting an AF event, a rate of change $(\Delta X/\Delta t)$ of cardiac intervals or heart rate can be detected within a time interval (e.g., 1-5 second) or within a plurality of beats (e.g., 3-10 beats), and $W_D$ can begin when $\Delta X/\Delta t$ falls below a respectively specified threshold. The detection window $W_D$ can have a specified length $L_{WD}$ for detecting sustentation of the target physiologic event. In an example, $L_{WD}$ can be approximately 400-800 beats.

The beats in the detection window $W_D$ can be classified in one of first two or more pre-defined beat classes, such as based variability of cardiac interval (CI). In an example, the variability of CI can be computed as beat-to-beat difference, i.e., $\Delta CI(i)=CI(i)-CI(i-1)$, where CI(i) denotes the cardiac interval at beat "i" and CI(i-1) denotes the cardiac interval at the previous beat "i-1". A beat can be classified as a stable beat if $\Delta CI(i)$ or $\Delta HR(i)$ falls within a first range, such as $|\Delta HR(i)|<5$ bpm. A beat can be classified as an unstable beat if $\Delta CI(i)$ or $\Delta HR(i)$ falls within a second range, such as $|\Delta HR(i)|>5$ bpm. A beat can be classified as a random beat if $CI(i)<CI(i-1)$ and $\Delta HR(i)<-5$ bpm. In another example, beat classification can be based on two or more variability measures, such as $\Delta CI(i)$ and $\Delta CI(i+1)$. A beat can be classified as a stable beat if $\Delta CI(i)$ or $\Delta HR(i)$ falls within a first range and $\Delta CI(i+1)$ or $\Delta HR(i+1)$ falls within a second range, such as $|\Delta HR(i)|<5$ bpm and $|\Delta HR(i+1)|<5$ bpm. A beat can be classified as an unstable beat if $\Delta CI(i)$ or $\Delta HR(i)$ falls within a third range and $\Delta CI(i+1)$ or $\Delta HR(i+1)$ falls within a fourth range, such as $|\Delta HR(i)|>5$ bpm and $|\Delta HR(i+1)|>5$. A beat can be classified as a random beat if $\Delta HR(i)<-5$ bpm and $\Delta HR(i+1)<-5$ bpm.

At 516, one or more relative quantities, such as a difference, a ratio, a proportion, or a percentage, can be computed among beat counts in the beat classes. The beat counts of the stable beat class, the unstable beat class, and the random beat class can be denoted by $N_S$, $N_U$, and $N_R$, respectively. A first ratio between $N_U$ and $N_S$ (i.e., $N_U/N_S$) and a second ratio between $N_R$ and a sum of $N_S$ and $N_U$ (i.e., $N_R/(N_S+N_U)$) can be computed.

At 518, the relative quantities can be compared to respectively specified criterion to detect the target AF event. An AF event is deemed detected, and a detected indication is generated, if the first ratio $N_U/N_S$ exceeds a first detection threshold $TH_{D1}$, and the second ratio $N_R/(N_S+N_U)$) exceeds a second detection threshold $TH_{D2}$. An example of $TH_{D1}$ is approximately between 3 and 5. An example of $TH_{D2}$ is approximately between 1-10%.

If the relative quantities fail to meet the specified detection criterion at 518, then no AF event is deemed detected, and additional cardiac electrical or mechanical signals can be sensed at 510. If the relative quantities meet the specified detection criterion at 518, then a confirmation process can begin at 520, where a confirmation window $W_R$ can be determined. The confirmation window $W_R$ can have a length $L_{WR}$ that is shorter than the length $(L_{WD})$ of the detection window $W_D$, such that $W_R$ is completely within the first data window $W_D$. For example, $W_R$ can be initiated at a specified time such that $W_R$ can be temporally located at a specified location within $W_D$. In an example, $W_D$ has a length of 500 cardiac intervals, and $W_R$ can include last 100 beats of the $W_D$. In an example, the confirmation window $W_R$ can start after the end of the detection window $W_D$.

At 522, one or more relative quantities can be computed using beat counts of various beat classes. The beats within the confirmation window $W_R$ can be classified into one of second two or more pre-determined beat classes each defined by a respective range of a signal feature. In an example, the second two or more beat classes can includes one or more of the first two or more beat classes. For example, the second beat classes can include one or more of the stable beat classes, unstable beat classes, or random beat classes, which are based on variability or pattern of cardiac cycles. In another example, the second two or more beat classes can include at least one beat class different than the first two or more beat classes. For example, the second two or more beat classes can be obtained by comparing a characteristic heart rate (such as a central tendency of the heart rates in the second portion of the received physiologic signal) to one or more threshold values.

The relative quantities can include a first ratio between the beat count in the unstable beat class $N_U$ and the beat count in the stable beat class $N_S$ (i.e., $N_U/N_S$), and a second ratio between the beat count in the random beat class $N_R$ and a sum of $N_S$ and $N_U$ (i.e., $N_R/(N_S+N_U)$). In an example, other signal features and associated criteria, different than or in addition to those used for detecting the target event, can be used to confirm the detected physiologic event. These additional or alternative signal features and criteria are selected such that the confirmation process has a higher sensitivity or a higher specificity than the detection process. For example, the confirmation window $W_R$ can be determined from a physiologic signal different from that used for target event detection, and the signal features extracted from the different physiologic signal can be used to confirm the detected AF event.

At 524, the relative quantities can be checked against respectively specified criterion. For example, if the first ratio $N_U/N_S$ exceeds a first confirmation threshold $TH_{R1}$, and the second ratio $N_R/(N_S+N_U)$ exceeds a second confirmation threshold $TH_{R2}$, an detected AF event is confirmed, and a data storage trigger signal can be generated at 526. In an example, the confirmation thresholds ($TH_{R1}$ or $TH_{R2}$) can be approximately identical to the corresponding detection thresholds ($TH_{D1}$ or $TH_{D2}$). In another example, at least one of the confirmation thresholds can be different than the corresponding detection threshold. If the relative quantities fail to meet the specified criterion, then a new confirmation process can be started at 520.

In an example, two or more non-identical confirmation windows $W_{R1}, W_{R2}, \ldots, W_{RK}$ can be created at 520. Each confirmation window, $W_{Ri}$, can be temporally located at a specified location within the detection window $W_D$. The beginning or the length of each confirmation window $W_{Ri}$ can be respectively determined using the method as discussed above for single confirmation window. The confirmation windows can have identical or different lengths. In an example, at least one confirmation window, $W_{Rp}$ overlaps in time with at least another confirmation window $W_{Rq}$. In another example, no two confirmation windows overlap in time. In an example, the K confirmation windows can span from the beginning to the end of the detection window $W_D$, such as by sweeping through the $W_D$. Relative quantities of beat counts in the beat classes can be computed for each of the two or more confirmation window at 522, and a respective partial confirmation indication can be generated by comparing the relative quantities to the respective confirmation criterion at 524.

At 526, a data storage trigger signal can be generated, such as in response to the detection indication of the target event and that the confirmation indication meeting a specified criterion. Similar to step 440 with respect to FIG. 4, the data storage trigger signal can be generated further in response to the elapsed time from a previous data storage trigger signal exceeding a specified threshold, at a specified time or frequency, or according to an external user command, such as from the instruction receiver circuit 250, that modifies, augments, or overrides the data storage trigger signal. When multiple confirmation windows $W_{R1}, W_{R2}, \ldots, W_{RK}$ are used in confirming the detected physiologic event, a plurality of partial confirmation indication $D_1, D_2, \ldots, D_K$, corresponding to the confirmation windows, can be generated, such as using similar method as discussed above. The $D_1, D_2, \ldots, D_K$ can then be combined to generate the confirmation indication, such as using a linear or a nonlinear combination of the one or more partial confirmation indications.

At 528, physiologic information can be stored in a memory, such as in response to the data storage trigger signal. As discussed above such as with respect to step 450 of FIG. 4, the physiologic information can include specified portion of the received physiologic signal, such as the first or second portion of the received physiologic signal used respectively for target event detection and confirmation, or physical or physiologic data different than the received physiologic signal, diagnostic data, or device functionality data associated with the detected and confirmed physiologic event.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a signal receiver circuit, configured to receive a physiologic signal obtained from a subject;
   a physiologic event detector circuit, configured to detect a target physiologic event using a first portion of the received physiologic signal;
   a data storage decision circuit, coupled to the signal receiver circuit and the physiologic event detector circuit, configured to:
      confirm the target physiologic event using a second portion of the received physiologic signal, the second portion including at least part of the first portion of the received physiologic signal; and
      generate a data storage trigger signal using the detection and the confirmation of the target physiologic event; and
   a controller circuit, coupled to the data storage decision circuit, configured to store in a memory in response to the data storage trigger signal, physiologic information associated with the confirmed target physiologic event.

2. The system of claim 1, wherein the first portion includes a first data window of the received physiologic signal, and the second portion includes a second data window temporally located at a specified location within the first data window.

3. The system of claim 2, wherein the second data window is temporally located within a latter half of the first data window.

4. The system of claim 1, wherein the first portion includes a first data window of the received physiologic signal, and the second portion includes second two or more non-identical data windows each temporally located at a respectively specified location within the first data window.

5. The system of claim 4, wherein the data storage decision circuit is configured to produce the confirmation of the physiologic event using one or more partial confirmation indications each generated using respective one of the second two or more data windows of the received physiologic signal.

6. The system of claim 1, wherein the signal receiver circuit is coupled to a sensor configured to sense cardiac electrical or mechanical activity, and the signal receiver circuit is configured to generate a signal indicative of heart rate (HR) or cardiac interval (CI) using the cardiac electrical or mechanical activity.

7. The system of claim 1, wherein the physiologic event detector circuit is configured to:
   classify cardiac intervals within the first portion of the received physiologic signal into one of first two or more beat classes, each of the first two or more beat classes including respective beat count; and
   detect the target physiologic event in response to t beat counts of the first two or more beat classes meeting a specified criterion.

8. The system of claim 7, wherein:
   the first two or more beat classes includes two or more of a stable beat class, an unstable beat class, or a random beat class; and
   the physiologic event detector circuit is configured to detect the target physiologic event in response to a relative quantity among the beat counts of the first two or more beat classes falling within a specified range, the relative quantity including a ratio or a proportion.

9. The system of claim 8, wherein the physiologic event detector circuit is configured to compute a beat variability for each of the cardiac intervals within the first portion, and to classify the cardiac intervals within the first portion into one of the stable beat class, the unstable beat class, or the random beat class when the beat variability falls within a specified range.

10. The system of claim 1, wherein the data storage decision circuit is configured to:
    classify cardiac intervals within the second portion of the received physiologic signal into one of second two or more beat classes, each of the second two or more beat classes including a respective beat count; and
    generate the data storage trigger signal in response to the beat counts of the second two or more beat classes meeting a specified criterion.

11. The system of claim 1, wherein the physiologic event detector circuit is configured to detect the target physiologic event including a cardiac arrhythmia or progression of a chronic disease.

12. The system of claim 1, wherein the data storage decision circuit is configured to track time elapsed from a previous data storage trigger signal, and to generate the data storage trigger signal further in response to the elapsed time exceeding a specified threshold.

13. A method, comprising:
- receiving a physiologic signal obtained from a subject;
- detecting a target physiologic event using a first portion of the received physiologic signal;
- generating a confirmation indication of the target physiologic event using a second portion of the received physiologic signal, the second portion including at least part of the first portion of the received physiologic signal;
- generating a data storage trigger signal using the detection and the confirmation of the target physiologic event; and
- storing in a memory in response to the data storage trigger signal, physiologic information associated with the confirmed target physiologic event.

14. The method of claim 13, wherein the first portion includes a first data window of the received physiologic signal, and the second portion includes a second data window temporally located at a specified location within the first data window.

15. The method of claim 13, wherein receiving the physiologic signal includes receiving a signal indicative of heart rate (HR) or cardiac interval (CI).

16. The method of claim 13, wherein detecting the target physiologic event includes detecting a cardiac arrhythmia or progression of a chronic disease.

17. The method of claim 13, wherein detecting a target physiologic event includes:
- computing cardiac cycles within the first data window of the received physiologic signal;
- classifying the cardiac cycles into one of first two or more beat classes, each of the first two or more beat classes including a respective beat count; and
- detecting the target physiologic event includes detecting the target physiologic event in response to the beat counts of the first two or more beat classes meeting a specified criterion.

18. The method of claim 17, wherein the first two or more beat classes includes two or more of a stable heat class, an unstable heat class, or a random beat class, and wherein detecting the target physiologic event include computing a relative quantity among the counts of the first two or more beat classes, and detecting the target physiologic event in response to the relative quantity falling within a specified range, the relative quantity including a ratio or a proportion.

19. The method of claim 13, wherein:
- generating a confirmation indication of the target physiologic event includes:
  - computing cardiac cycles within the second portion of the received physiologic signal;
  - classifying the cardiac cycles into one of second two or more beat classes, each of the second two or more beat classes including a respective beat count; and
- generating the data storage trigger signal includes generating the data storage trigger signal in response to the beat counts of the second two or more beat classes meeting a specified criterion.

20. The method of claim 13, wherein the first portion includes a first data window of the received physiologic signal, and the second portion includes second two or more non-identical data windows each temporally located at a respectively specified location within the first data window, and wherein generating the confirmation indication includes:
- generating one or more partial confirmation indications using respective one of the second two or more data windows of the received physiologic signal;
- generating the confirmation indicating using a fusion of the one or more partial confirmation indications.

* * * * *